United States Patent [19]

Wiskott

[11] 4,261,895
[45] Apr. 14, 1981

[54] ALKANOYL-PROLINE DERIVATIVES AND HOMOLOGUES THEREOF

[75] Inventor: Erik Wiskott, Bottmingen, Switzerland

[73] Assignee: Sandoz Ltd., Basel, Switzerland

[21] Appl. No.: 953,565

[22] Filed: Oct. 23, 1978

[30] Foreign Application Priority Data

Oct. 28, 1977 [CH] Switzerland ............... 13153/77

[51] Int. Cl.³ .......................................... C07D 405/12
[52] U.S. Cl, .......................... 260/326.36; 260/239 A; 260/326.14 R; 260/326.25; 260/326.34; 260/326.35; 260/326.37; 260/326.43; 424/244; 424/258; 424/263; 424/267; 424/274; 424/275; 424/285; 546/147; 546/170; 546/193; 546/196; 546/201; 546/202; 546/208; 546/212; 546/214; 546/227; 546/245
[58] Field of Search ............ 260/326.43, 326.36, 260/239 AR; 546/214, 227; 424/274

[56] References Cited

U.S. PATENT DOCUMENTS 4,046,889 9/1977 Ondetti ........................... 424/244
4,217,458 8/1980 Ondetti et al. ................. 260/326.43

OTHER PUBLICATIONS

Burger, A. "Medincinal Chemistry", 2nd ed., Interscience Publishers, Inc., 1960. pp. 42–43.

*Primary Examiner*—Mary C. Lee
*Attorney, Agent, or Firm*—Gerald D. Sharkin; Robert S. Honor; Timothy G. Rothwell

[57] ABSTRACT

The compounds of formula I

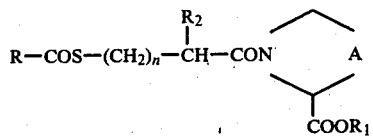

wherein
R is
(a) hydrogen,
(b) cycloalkyl of 3 to 7 carbon atoms,
(c) alkyl of 2 to 5 carbon atoms monosubstituted by hydroxy, with the proviso that the hydroxyl radical is separated by at least 2 carbon atoms from the carbonylthio moiety to which R is bound,
(d) phenyl or phenylalkyl of 7 to 11 carbon atoms, each monosubstituted or independently disubstituted in the phenyl ring by alkyl of 1 to 4 carbon atoms or halogen of atomic number of from 9 to 35, or phenyl or phenylalkyl of 7 to 11 carbon atoms, each monosubstituted or independently disubstituted or independently trisubstituted in the phenyl ring by alkoxy of 1 to 4 carbon atoms, or
(e) furyl, benzo[b]furyl, thienyl, benzo[b]thienyl, pyridyl, quinolyl, isoquinolyl, 2- or 3-pyrrolyl or indolyl other than 1-indolyl, $R_1$ and $R_2$ independently are hydrogen or alkyl of 1 to 4 carbon atoms, A is ethylene optionally monosubstituted by hydroxy, or methylene or trimethylene and n is 0, 1 or 2, are useful as antihypertensive agents.

2 Claims, No Drawings

ALKANOYL-PROLINE DERIVATIVES AND HOMOLOGUES THEREOF

The present invention relates to 1-alkanoyl-proline derivatives and homologues thereof.

In accordance with the invention there are provided compounds of formula I

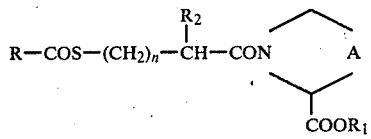

wherein
R is
(a) hydrogen,
(b) cycloalkyl of 3 to 7 carbon atoms,
(c) alkyl of 2 to 5 carbon atoms monosubstituted by hydroxy, with the proviso that the hydroxy radical is separated by at least 2 carbon atoms from the carbonylthio moiety to which R is bound,
(d) phenyl or phenylalkyl of 7 to 11 carbon atoms, each monosubstituted or independently disubstituted in the phenyl ring by alkyl of 1 to 4 carbon atoms or halogen of atomic number of from 9 to 35, or phenyl or phenylalkyl of 7 to 11 carbon atoms, each monosubstituted or independently disubstituted or independently trisubstituted in the phenyl ring by alkoxy of 1 to 4 carbon atoms, or
(e) furyl, benzo[b]furyl, thienyl, benzo[b]thienyl, pyridyl, quinolyl, isoquinolyl, 2- or 3-pyrrolyl or indolyl other than 1-indolyl, $R_1$ and $R_2$ independently are hydrogen or alkyl of 1 to 4 carbon atoms,
A is ethylene optionally monosubstituted by hydroxy, or methylene or trimethylene and
n is 0, 1 or 2.

In one group of compounds R has significance (a); in another group R has significance (b); in another group significance (c); in another group significance (d); in another group significance (e); in another group R is furyl; in another benzo[b]furyl; in another thienyl; in another benzo[b]thienyl; in another pyridyl; in another quinolyl; in another isoquinolyl; in another pyrrolyl; in another indolyl.

R preferably has significance (d) or (e), especially (e). $R_1$ preferably is hydrogen. $R_2$ preferably is alkyl. A preferably is optionally substituted ethylene, especially unsubstituted. n preferably is 1.

Cycloalkyl preferably is of 3,5 or 6, especially 5 or 6 carbon atoms. Alkyl monosubstituted by hydroxy preferably is of 2 or 3, especially 2 carbon atoms. When R has significance (c), the hydroxy group preferably is in the distal terminal position. Phenylalkyl preferably is of 6 or 7 carbon atoms, and especially it is benzyl. When the phenylalkyl group is of more than 8 carbon atoms, it preferably is branched in the alkylene moiety thereof, especially in the position α to the carbonyl moiety to which R is bound, as in the group—$C(CH_3)_2$—$C_6H_5$ or —$C(CH_3)_2$—$CH_2$—$C_6H_5$. When the phenyl or phenylalkyl group is monosubstituted, the substituent preferably is in the 4 position. When it is disubstituted, the substituents preferably are in the 3 and 4 positions. When it is trisubstituted, the substituents preferably are in the 3,4 and 5-positions. When it is di- or trisubstituted, the substituents preferably are identical. When R is di- or trisubstituted phenyl, preferably at least one of the 2 and 6 positions is unsubstituted. Alkyl and alkoxy preferably are of 1 or 2, especially 1 carbon atoms. Halogen preferably is chlorine or bromine, especially chlorine. The phenyl or phenylalkyl group conveniently is di- or trisubstituted.

Significance (e) preferably is monocyclic. When it is bicyclic, the bond to the carbonylthio moiety preferably is attached to a ring carbon atom of the heterocyclic moiety. When R contains a five-membered heterocycle, it preferably is bound to the carbonylthio moiety with a carbon atom in a position adjacent to the heteroatom. When R contains an six-membered heterocycle, it preferably is bound to the carbonylthio moiety through a ring carbon atom in a position adjacent to the heteroatom or one ring carbon atom further removed from it, especially the former.

When A is ethylene monosubstituted by hydroxy, the carbon atom substituted by the hydroxyl radical preferably is separated by one methylene radical from the carbonyloxy radical.

In accordance with the invention, a compound of formula I may be obtained by a process comprising reacting a compound of formula II

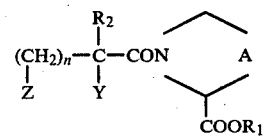

wherein $R_1$, $R_2$ and A are as defined above and either (i) n is 0, 1 or 2, Y is hydrogen and Z is a leaving group or (ii) n is 1 and Y and Z are together a bond, with a compound of formula III

R—COSH    III wherein R is as defined above.

The present process may be effected in conventional manner. When Y is hydrogen, it may e.g. be effected under conditions analogous to the conditions for nucleophilic substitution with a thiocarboxylic acid acting on an amide of an alkyl carboxylic acid which is substituted in the distal terminal position with a leaving group. Suitable reaction temperatures may be from about 0° C. to about 100° C., preferably room temperature. The reaction is preferably effected in a suitable inert organic solvent, such as ether, methylene chloride, chloroform, benzene or toluene. Optionally an excess of a compound of formula III may be used as solvent. The thiocarboxylic acid is especially reacted in anionic form, e.g. in alkali metal salt form. Z is e.g. halogen, preferably chlorine or bromine, or a group $R_z$—$SO_2$—O—, wherein $R_z$ is phenyl, tolyl or lower alkyl. Z especially is chlorine.

When Y and Z together are a bond, preferably reaction conditions analogous to known conditions for the 1,4-addition of a thiocarboxylic acid to an acryloyl derivative are used. The compounds of formula III are preferably reacted in anionic form, e.g. in alkali metal salt form.

Free acid forms of the compounds of formula I, wherein $R_1$ is hydrogen, may be converted into salt forms in conventional manner and vice-versa. Suitable bases for salt formation include sodium hydroxide, tert-butylamine and dicyclohexylamine.

In the compounds of formula I, the ring carbon atom which is substituted by the carbonyloxy radical is asymmetrically substituted. The compounds may thus exist in the racemic form or in individual optical isomer form. The preferred optical isomer has the S configuration at this asymmetrical substituted carbon atom.

When A is ethylene monosubstituted by hydroxy, the carbon atom substituted by the hydroxy radical also is asymmetrical substituted. The corresponding compounds may thus exist in the form of diastereoisomers. When the hydroxy radical is adjacent to the carbonyloxy radical, the preferred diastereoisomer has the S configuration at the carbon atom substituted by the hydroxy radical; when it is not adjacent, the preferred diastereoisomer has the R configuration at that carbon atom.

The corresponding optical isomers or diastereoisomers of the compounds of formula I may be obtained in known manner, e.g. by using corresponding, optically pure stereoisomers of the compounds of formula II, which may themselves be obtained from corresponding optically active starting materials.

When $R_2$ is alkyl, the carbon atom substituted by the $R_2$ radical also is asymmetrically substituted. The corresponding compounds may thus also exist in the form of diastereoisomers. The preferred diastereoisomer has the configuration indicated in formula IV at the carbon atom substituted by the radical $R_2$:

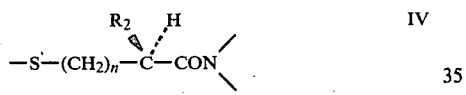

IV

The corresponding diastereoisomers of the compounds of formula I may be obtained in known manner, e.g. by fractional crystallization of a suitable salt, e.g. the tert. butyl ammonium or dicyclohexylammonium salt, or chromatography of the corresponding diastereoisomeric mixture.

A group of compounds of formula I has formula Ia

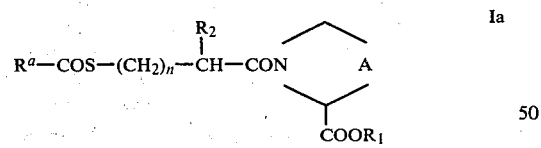

Ia wherein $R_1$, $R_2$, A and n are as defined above and $R^a$ has the significance (a), (b), (c) or (e) indicated above for R.

A preferred group of compounds of formula Ia has formula Iaa

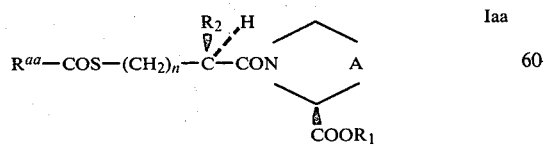

Iaa wherein $R_1$, $R_2$, A and n are as defined above and $R^{aa}$ has the significance (e) indicated above for R.

A preferred group of compounds of formula Iaa has formula Iaaa

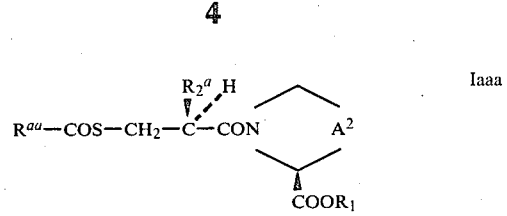

Iaaa wherein
$R_1$ and $R^{aa}$ are as defined above,
$R_2^a$ is alkyl of 1 to 4 carbon atoms and
$A^a$ is ethylene optionally monosubstituted by a hydroxy radical separated by a methylene radical from the carbon atom substituted by the carbonyloxy radical, the carbon atom substituted by the hydroxy radical having the R configuration.

Another group of compounds of formula I has formula Ib,

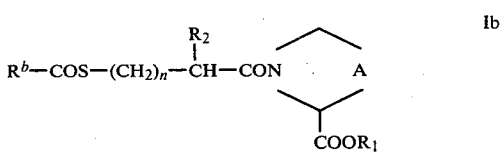

Ib wherein
$R_1$, $R_2$, A and n are as defined above and
$R^b$ has the significance (d) indicated above for R.

A preferred group of compounds of formula Ib has formula Iba

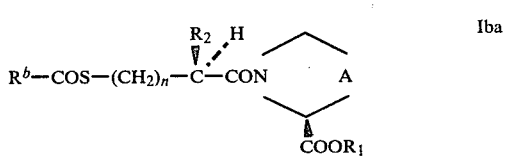

Iba wherein $R^b$, $R_1$, $R_2$, A and n are as defined above.

A preferred group of compounds of formula Iba has formula Ibaa

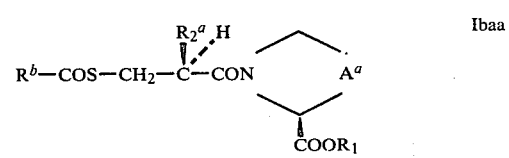

Ibaa wherein $R^b$, $R_1$, $R_2^a$ and $A^a$ are as defined above.

The production of the starting materials may be effected in a manner analogous to known methods.

A compound of formula IIIa

IIIa wherein $R^f$ has significance (e) indicated above for R, may e.g. be obtained by reacting the corresponding carboxylic acid with ethyl chloroformate and treating the mixed anhydride so obtained with $H_2S$.

Insofar the preparation of any starting material is not particularly described, this may be effected in conventional manner.

In the following examples all temperatures are in degrees Centigrade and are uncorrected.

Where the compound is designated as a (RS) mixture with respect to the carbon atom carrying R₂, this is approximately a 1:1 mixture.

EXAMPLE 1

(2S)-1-[(2RS)-3-(2-furancarbonylthio)-2-methyl-propanoyl]-2-pyrrolidine carboxylic acid 11.4 g (2S)-1-(2- methyl-2-propenoyl)-2-pyrrolidine carboxylic acid are dissolved in 16.5 ml ethanol and 10 g furan-2-thiocarboxylic acid are added dropwise over 15 minutes. The reaction mixture is stirred overnight at room temperature, and methylene chloride and water (9:1) are then added. The so obtained organic phase is decanted and extracted with 0.5 N NaOH. The combined aqueous phases are adjusted to pH 4 and then twice extracted with 0.5 l $CH_2Cl_2$. The combined organic phases are dried over $MgSO_4$, filtered and the solvent is evaporated. The residue is dissolved in $CH_2Cl_2$/ether (1:4) and 6 ml tert-butylamine dissolved in ether are added; the tert-butyl ammonium salt of the title compound precipitates (M.P. 132°–140°) ($[\alpha]_D^{20} = -67.3°$; c=2.2 in $H_2O$).

After further recrystallisation of the tert. butyl ammonium salt or dicyclohexylammonium salt in known manner, the individual R and S forms are obtained.

The following compounds of formula I may be obtained in a manner analogous to Example 1, using the corresponding starting materials of formula III and of formula II (when n is 1, Y and Z together are a bond; when n is 0, 1 or 2, Y is hydrogen and Z is chlorine).

| Ex. No. | R | $R_1^{(a)}$ | $R_2$* | A | n | M.P. |
|---|---|---|---|---|---|---|
| 2 | CH₃O—⟨phenyl⟩—OCH₃ 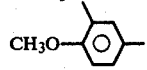 | —H (S) | —CH₃ | —CH₂CH₂— | 1 | dch** 212–215° |
| 3 | ⟨thienyl-S⟩  | —H (S) | —CH₃ | —CH₂CH₂— | 1 | |
| 4 | ⟨N-phenyl-O⟩  | —H (S) | —CH₃ | —CH₂CH₂— | 1 | |
| 5 | ⟨O-phenyl-NH⟩ 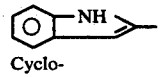 | —H (S) | —CH₃ | —CH₂CH₂— | 1 | |
| 6 | Cyclobutyl | —H (S) | —CH₃ | —CH₂CH₂— | 1 | |
| 7 | ⟨O-phenyl-O⟩ 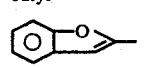 | —H (S) | —CH₃ | —CH₂CH₂— | 1 | | dch = dicyclohexyl ammonium salt
(a)(R), (S) and (RS) refer to the absolute configuration at the carbon atom to which the group —COOR₁ is bound.
*Each of the Example 2 to 7 compounds are obtained in (RS) form, R form and S form.
**(RS) form.

| Ex. | R | $R_1^{(a)}$ | $R_2^{(a)}$ | A | n |
|---|---|---|---|---|---|
| A | 2-hydroxyethyl | —H (S) | isopropyl (RS) | 2-hydroxy-ethylene (b)(c) | 1 |
| B | cyclopropyl | tert-butyl (R) | —H | trimethylene | 1 |
| C | 3-quinolyl | —H (S) | tert-butyl (RS) | methylene | 2 |
| D | —H | ethyl (S) | methyl (S) | 1-hydroxy-ethylene (c)(f) | 2 |
| E | cycloheptyl | ethyl (RS) | ethyl (RS) | 2-hydroxy-ethylene (b)(e) | 2 |
| F | 2,4,6-tri-methoxyphenyl | ethyl (S) | isopropyl (R) | trimethylene | 2 |
| G | 2-methyl-4-(3-isopropyl-5-bromophenyl)-2-butyl | —H (RS) | —H | 1-hydroxy-ethylene (d)(f) | 0 |
| H | 3,5-di-tert-butylbenzyl | isopropyl (RS) | tert.butyl (RS) | ethylene | 0 |
| I | 4-chloro-3-fluorophenyl | methyl (R) | methyl (RS) | trimethylene | 1 |
| J | 3-(3-tert-butyl-phenyl)-2-propyl | —H (RS) | ethyl (RS) | methylene | 2 |
| K | 3-pyrrolyl | ethyl (RS) | —H | 2-hydroxy-ethylene (b)(d) | 1 |
| L | 7-benzo[b]thienyl | ethyl (RS) | —H | trimethylene | 1 |
| M | 4-pyridyl | tert-butyl (RS) | isopropyl (R) | methylene | 2 |
| N | 4-isoquinolyl | —H (S) | isopropyl (S) | 1-hydroxy-ethylene (c)(f) | 2 |

(a)(R), (S) and (RS) refer to the absolute configuration at the carbon atom which the group —COOR₁ or R₂ is bound.
(b)The hydroxy radical is not adjacent to the carbonyloxy radical.
(c)The carbon atom substituted by the hydroxy radical has the (R) configuration.
(d)The carbon atom substituted by the hydroxy radical has the (S) configuration.
(e)The carbon atom substituted by the hydroxy radical is in (RS) form.
(f)The hydroxy radical is adjacent to the carbonyloxy radical.

The compounds of formula I are useful because they exhibit pharmacological activity in animals. They exhibit antihypertensive activity.

This is indicated in standard tests, e.g. in the Grollman rat test [A. Grollman, Proc.Soc.Exp.Biol. and Med. 57 (1944) 102] on p.o. administration of from about 1 to 100 mg/kg.

The compounds are therefore useful as antihypertensive agents, e.g. for the prophylaxis and treatment of conditions associated with a malfunction of the reninangiotensin system. Especially interesting in this indication is the compound of Example 1.

For this use the dosage will, of course, vary depending on the compound employed, mode of administration and treatment desired. However, in general, satisfactory results are obtained when administered at a daily dosage of from about 1 mg to about 100 mg per kg animal body weight, conveniently given in divided doses 2 to 4 times a day or in sustained release form. For the larger mammals, the total daily dosage is in the range from about 50 to about 1000 mg, and dosage forms suitable for oral administration comprise from about 12 mg to about 500 mg of the compounds admixed with a solid or liquid pharmaceutical carrier or diluent.

When R₁ is hydrogen, the compounds of formula I may be administered in pharmaceutically acceptable salt form. Such salt forms exhibit the same order of activity as the free forms.

The present invention also provides a pharmaceutical composition comprising a compound of formula I, in free form or, when R₁ is hydrogen, alternatively in pharmaceutically acceptable salt form, in association with a pharmaceutical carrier or diluent. Such compositions may be in the form of, for example, a solution or a tablet.

I claim:
1. A compound of the formula

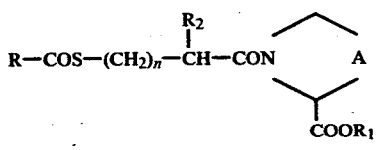

wherein
R is furyl, and $R_1$ and $R_2$ independently represent hydrogen or alkyl of 1 to 4 carbon atoms, and A is ethylene optionally monosubstituted by hydroxy or methylene or trimethylene, and n is 0, 1 or 2, in free form or when $R_1$ is hydrogen in pharmaceutically acceptable salt form.

2. The compound of claim 1 which is 2(S)-1-[(2RS)-3-(2-furancarbonylthio)-2-methylpropanoyl]-2-pyrrolidine carboxylic acid.

* * * * *